United States Patent [19]

Couch, Jr.

[11] Patent Number: 4,567,887
[45] Date of Patent: Feb. 4, 1986

[54] THERAPEUTIC DEVICE FOR PREVENTION AND TREATMENT OF DECUBITOUS ULCERATIONS

[76] Inventor: Thomas E. Couch, Jr., 17 White Fir Dr., Loudonville, N.Y. 12211

[21] Appl. No.: 715,952

[22] Filed: Mar. 25, 1985

[51] Int. Cl.$^4$ .............................................. A61F 13/00
[52] U.S. Cl. ................................ 128/132 R; 128/118; 5/431
[58] Field of Search ........ 128/132, 112, 118, DIG. 20, 128/117; 2/411, 413, 22, 23, 24, 267, DIG. 3; 5/431, 443

[56] References Cited

U.S. PATENT DOCUMENTS

| | | | |
|---|---|---|---|
| 920,683 | 5/1909 | Stevens | 128/117 |
| 1,468,072 | 9/1923 | Ogle | 128/DIG. 20 |
| 2,195,817 | 4/1940 | Johnson | 2/24 |
| 2,663,020 | 12/1953 | Cushman | 2/24 |
| 2,785,419 | 3/1957 | Walker | 5/431 |
| 3,052,236 | 9/1962 | Schrieber | 128/118 |
| 3,158,878 | 12/1964 | Pernell | 5/431 |
| 3,171,410 | 3/1965 | Towle et al. | 128/118 |

FOREIGN PATENT DOCUMENTS 1206361 9/1970 United Kingdom ................ 128/118

Primary Examiner—Gene Mancene
Assistant Examiner—John Weiss
Attorney, Agent, or Firm—Walter F. Wessendorf, Jr.

[57] ABSTRACT

Disclosed is a therapeutic device for the prevention and treatment of ulcerations in the hip and coccygeal areas. Tubular members surround and continuously make contact with second areas adjacent to and surrounding the immediate areas of the bony prominences of the hip and coccygeal areas.

Also disclosed is a therapeutic device for the prevention and treatment of ulcerations in the scapular area. Tubular members surround and continuously make contact with second areas adjacent to and surrounding the immediate areas of the bony prominences of the scapular area.

Also disclosed is a therapeutic device for the prevention and treatment of ulcerations in the elbow area. A tubular member surrounds and continuously makes contact with a second area adjacent to and surrounding the immediate area of the bony prominence of the elbow.

19 Claims, 19 Drawing Figures

THERAPEUTIC DEVICE FOR PREVENTION AND TREATMENT OF DECUBITOUS ULCERATIONS

BACKGROUND

1. Technical Field

This invention relates to a therapeutic device for the prevention and treatment of ulcerations in various parts of the body.

2. Background

Ulcerations commonly referred to as bed sores and other pressure related wounds which develop when a patient is bed-ridden or immobile for considerable periods of times such as when confined to a wheel chair. Such ulcerations usually appear at the location of bony prominences due to the concentration of pressure caused at these points.

There is a need for a device to prevent pressure over the coccyx and the bony prominence on the posterior aspect of the coccyx bone. There is a need for another device to protect the scapular areas from the development of decubitous ulcers. And there is a need for another device to protect the elbow areas from decubitous ulcers.

SUMMARY OF THE INVENTION

Accordingly, the object of the invention is to provide devices for the prevention of ulcerations of the coccygeal and hip areas, the scapular area and the elbows, respectively, with such devices comprising tubular members of resilient material suitably shaped to generally develop the corresponding anatomical areas of consideration and having openings into which the bony prominences protrude to relieve and eliminate the pressures normally experienced at such points of bony prominences of the patient's coccygeal and hip areas, scapular areas and elbows, respectively, while at the same time leave such bed-ridden or chair-ridden patient free to assume any desired position without interfering with the effectiveness of any of such devices.

BRIEF DESCRIPTION OF THE DRAWINGS

This object and other objects of the invention should be discerned and appreciated by reference to the drawings, wherein like reference numerals refer to similar parts throughout the several views, in which.

DESCRIPTION OF THE PREFERRED EMBODIMENT

Figure 1:
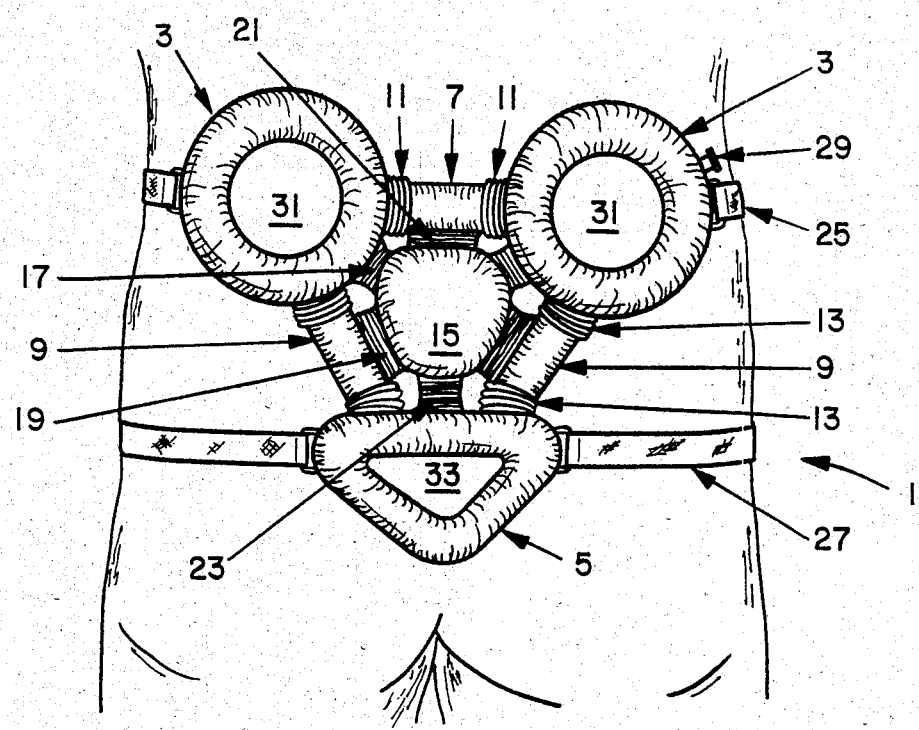
FIG. 1 is a front view of the device for the coccygeal and hip areas, with the tubular members for the hip areas being circular-shaped and the tubular member for the coccygeal area being triangular-shaped.

In FIG. 1 of the drawings, reference numeral 1 generally refers to the therapeutic device for use in the coccygeal and hip areas for the prevention and treatment of ulcerations. Device 1 has two circular-shaped tubular members 3 and a triangular-shaped tubular member 5. Tubular members 3 are joined and communicate with each other via interposed tubular connecting element 7; and tubular members 3 are joined and communicate with tubular member 5 via interposed tubular connecting element 9. The ends 11 of tubular connecting element 7 are of accordion-like configuration and the ends 13 of tubular connecting element 9 are of accordion-like configuration. A hollow bladder element 15 is joined to the tubular members 3 via accordion-like webbing 17, is joined to the tubular connecting elements 9 via accordion-like webbing 19, is joined to and communicates with the tubular connecting element 7 via accordion-like tubular connecting element 21 and is joined to and communicates with the tubular member 5 via accordion-like tubular connecting element 23. An adjustable attachment element 25 of strip webbing with Velcro fasteners (not shown) is suitably affixed to the tubular members 3 and is disposed in mounting relationship about the hip area of the patient; and an adjustable attachment element 27 of strip webbing with Velcro fasteners (not shown) is suitably affixed to the tubular members 5 and is disposed in mounting relationship about the buttocks region of the patient. The accordion-like end 11 and 13, the accordion-like webbing 17 and 19, and the accordion-like tubular connecting elements 21 and 23, function to allow the device to fit and to be adjusted for variations in the anatomy in the event that, in different patients, the bony prominences in the hip area are wider apart or the bony prominences in the coccygeal area are higher or lower. Valve 29 allows the introduction of air to thereby fill up the tubular members 3 and 5, the tubular connecting elements 7, 9, 21 and 23, and the bladder element 15. The device can be utilized without the bladder element 15; however, bladder element 15 allows the device 1 to seat itself better over the buttocks region with increased comfort along with aid in securement by virtue of fitting of natural contours via bladder element 15. The device can be inflated with liquid, semisolids or gas and is made of suitable material that is hypo-allergenic in nature.

Ulcerations appear and develop at the location of a bony prominence on a patient's body and the immediate area of such bony prominence, and such ulcerations are caused by direct contact pressure from an object such as a bed, wheel chair, furniture, etc. making the direct contact with such bony prominence and its immediate area as a result of such patient being bed-ridden, confined to a wheel chair or immobile for a period of time.

The tubular members 3 surround the bony prominences of the hip area and continuously make contact with second areas adjacent to and surrounding the immediate areas 31 of such bony prominences of the hip area and thereby transfer and spread to such second areas the pressures created and caused by direct contact with an object, such as a bed, wheel chair, furniture, etc. to thereby prevent ulcerations from developing which would otherwise develop from contact of such object with such bony prominences and the immediate areas 31 of such bony prominences. Likewise, the tubular member 5 surrounds the bony prominence of the coccygeal area and continuously makes contact with a second area adjacent to and surrounding such immediate area 33 of the bony prominence of such coccygeal area to thereby transfer and spread to such second area the pressures created and caused by direct contact with an object, such as a bed, wheel chair, furniture, etc. to thereby prevent ulcerations from developing which would otherwise develop from contact of such object with such bony prominence and the immediate area 33 of such bony prominence. Hence, with the therapeutic device 1 emplaced and worn by a patient, no ulcerations in the hip region and coccygeal area can be caused by contact pressure from an object. Similarly, the therapeutic device 1 can be utilized for the treatment of ulcerations theretofore developed by the patient as a result of contact pressures from an object.

Figure 2:
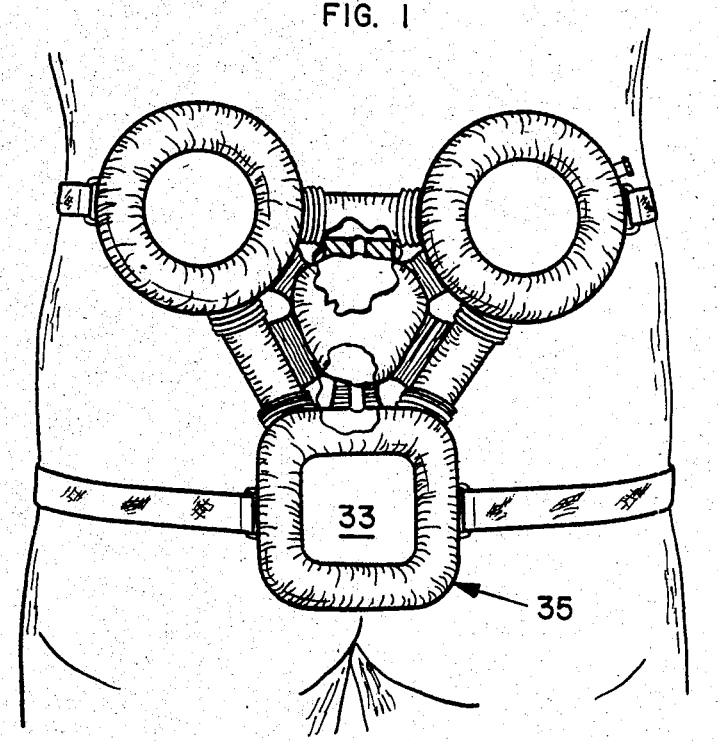
FIG. 2 is a front view of a modification of the device shown in FIG. 1 but with the tubular member for the coccygeal area being square-shaped.
Figure 3:
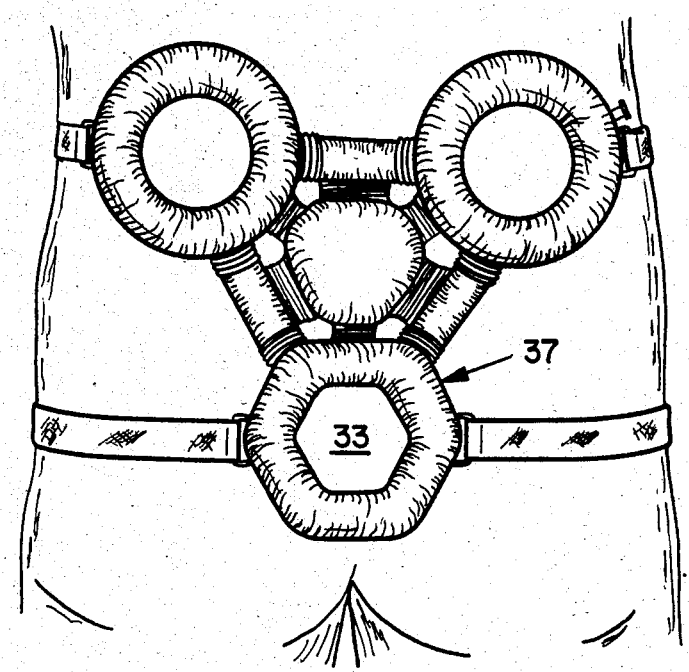
FIG. 3 is a front view of a modification of the device shown in FIG. 1 but with the tubular device for the coccygeal area being hexagonal-shaped.
Figure 4:
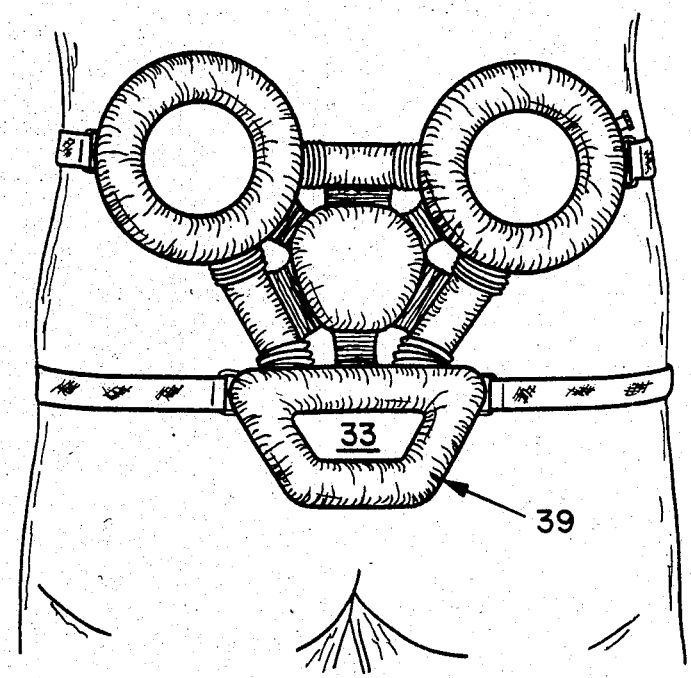
FIG. 4 is a front view of a modification of the device shown in FIG. 1 but with the tubular device for the coccygeal area being trapezoidal-shaped.

FIGS. 2-4 of the drawings differ from the therapeutic device 1 shown and described in FIG. 1 in that the shape of the tubular member has been changed to functionally and spatially accommodate the differences in the configurations of the bony prominences underlying the immediate area 33. In FIG. 2, a square-shaped tubular member 35 is used in place of the tubular member 5; in FIG. 3, a hexagonal-shaped tubular member 37 is used; and in FIG. 4, a trapezoidal-shaped tubular member 39 is used.

Figure 5:
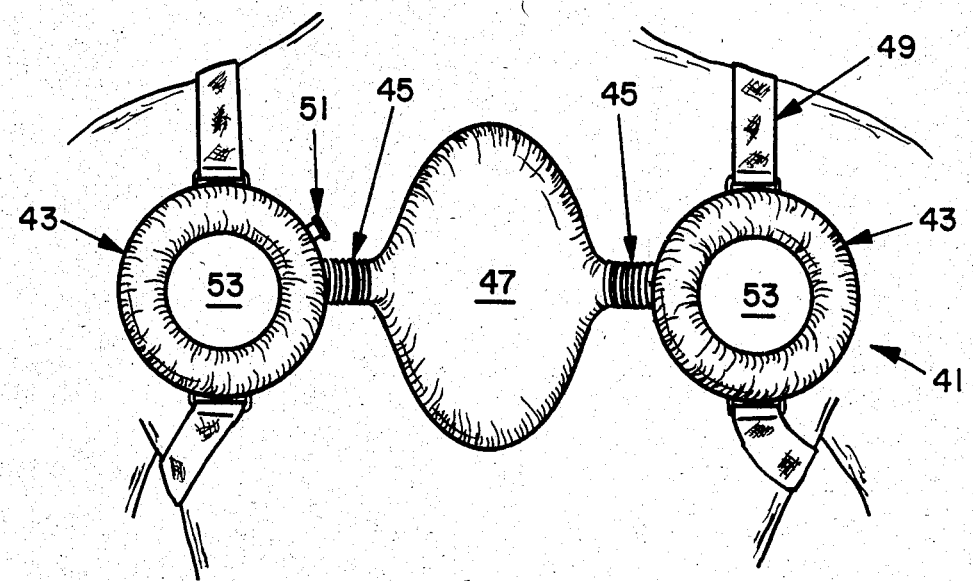
FIG. 5 is a front view of the device for the scapular area with the circular-shaped tubular members being joined by a bladder element.

In FIG. 5 of the drawings, reference numeral 41 generally refers to the therapeutic device for use in the scapular area for the prevention and treatment of ulcerations. Device 41 has two circular-shaped tubular members 43. Tubular members 43 are joined and communicate with each other via interposed accordion-like connecting elements 45 and hollow bladder element 47, with such bladder element 47 filling the natural dell between the scapulae. Adjustable attachment elements 49 of strip webbing with Velcro fasteners (not shown) are suitably affixed to the tubular members 43 and are disposed in mounting relationship by going over the shoulders and underneath the arms of the patient. Valve 51 allows inflation of the tubular members 43, connecting elements 45 and bladder element 47.

The tubular members 43 surround the bony prominences of the scapular area surround and continuously make contact with second areas adjacent to and surrounding the immediate areas 53 of such bony prominences of the scapular area and thereby transfer and spread to such second contact areas the pressures created and caused by direct contact with an object, such as a bed, wheel chair, furniture, etc. to thereby prevent ulcerations from developing which would otherwise develop from contact of such object with such bony prominences and the immediate areas 53 of such bony prominences. Hence, with therapeutic device 41 emplaced and worn by a patient, no ulcerations in the scapular area can be caused by contact pressure from an object. Similarly, therapeutic device 41 can be utilized for the treatment of ulcerations theretofore developed by a patient in the scapular area.

Figure 6:
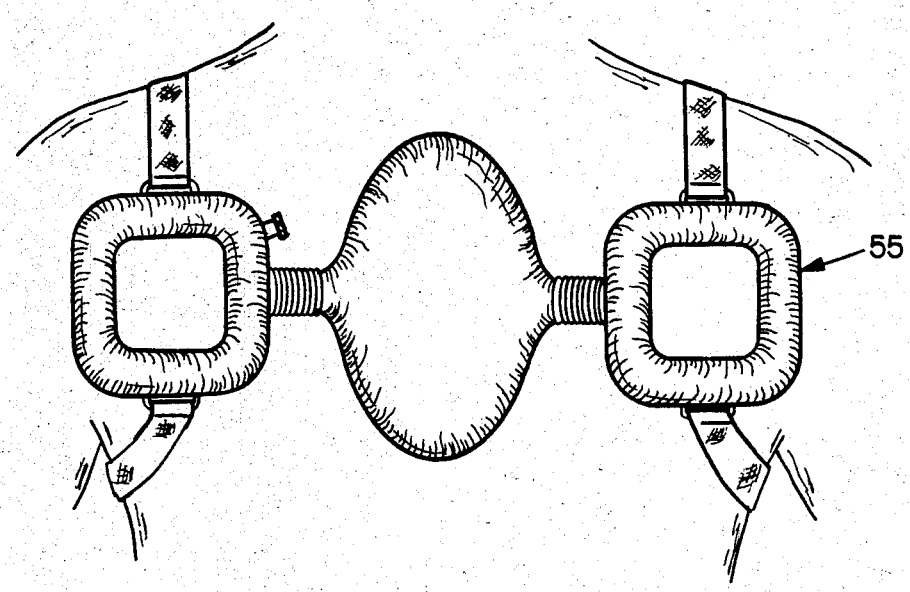
FIG. 6 is a front view of a modification of the device shown in FIG. 5 but with the tubular members being square-shaped.
Figure 7:
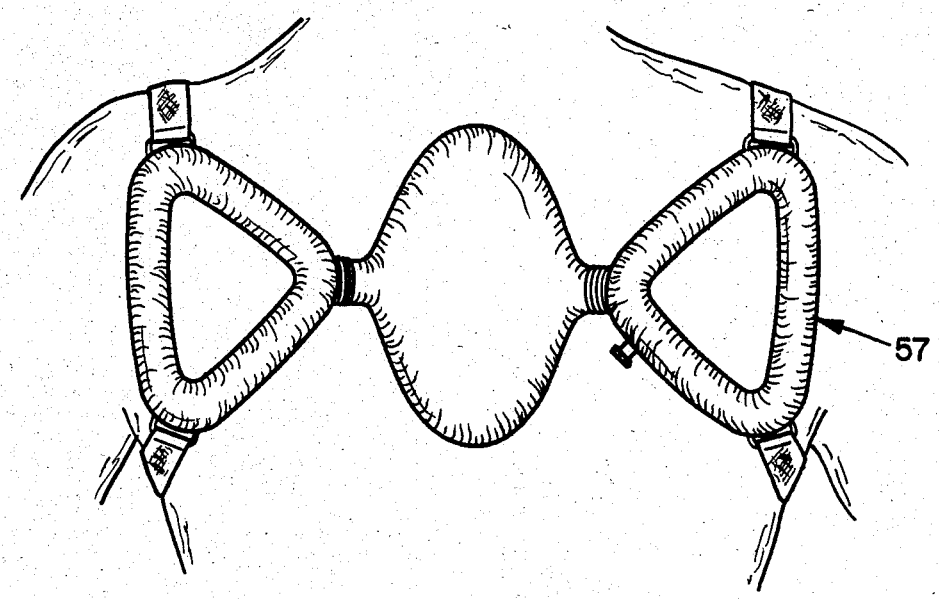
FIG. 7 is a front view of a modification of the device shown in FIG. 5 but with the tubular members being triangular shaped.
Figure 8:
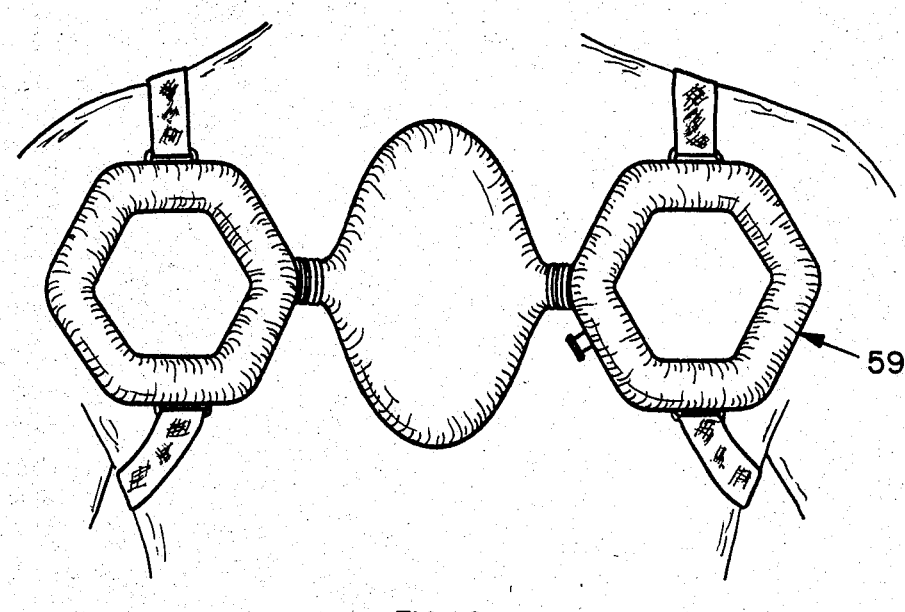
FIG. 8 is a front view of a modification of the device shown in FIG. 5 but with the tubular members being hexagonal-shaped.

FIGS. 6-8 of the drawings differ from the therapeutic device 41 shown and described in FIG. 5 in that the shape of the tubular member has been changed to functionally and spatially accommodate the differences in the configurations of the bony prominences underlying the immediate areas 53. In FIG. 6, an element 55 that is square-shaped is used in place of tubular member 43; in FIG. 7, a triangular-shaped tubular member 57 is used; and in FIG. 8, a hexagonal-shaped tubular member 59 is used.

Figure 9:
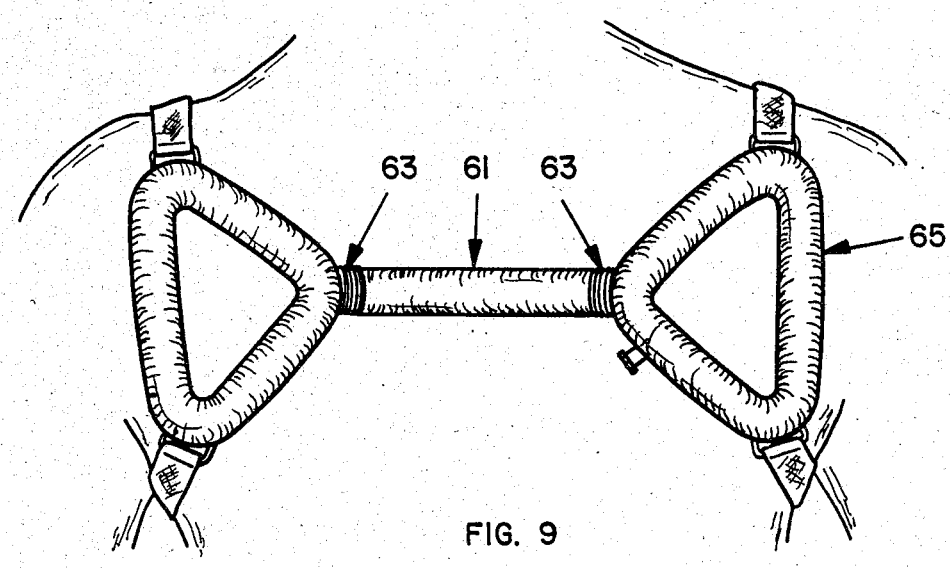
FIG. 9 is a front view of the device as shown in FIG. 7 but with the triangular-shaped tubular members being joined by a tubular connecting element instead of a bladder element.
Figure 10:
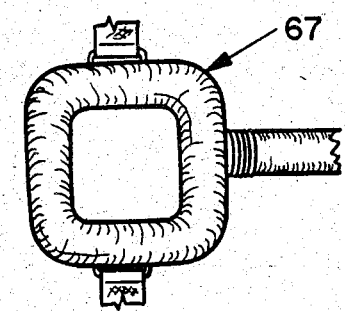
FIG. 10 shows the tubular members of FIG. 9 as being square-shaped.
Figure 11:
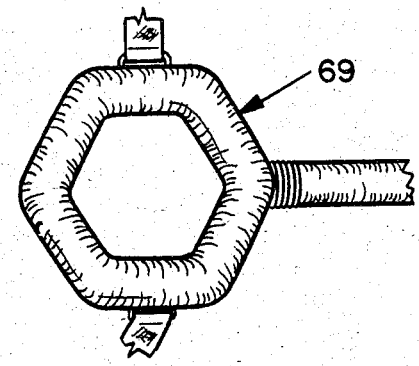
FIG. 11 shows the tubular members of FIG. 9 as being hexagonal-shaped.
Figure 12:
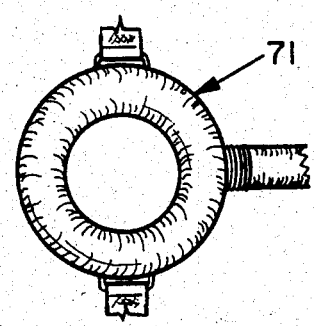
FIG. 12 shows the tubular members of FIG. 9 as being circular-shaped.
Figure 13:
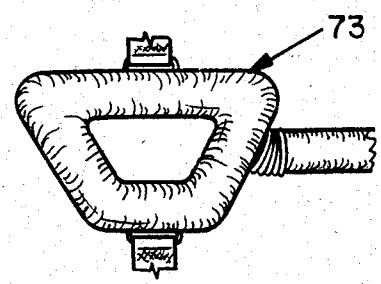
FIG. 13 shows the tubular members of FIG. 9 as being trapezoidal-shaped.

FIGS. 9-13 of the drawings differ further from the therapeutic device 41 shown and described in FIG. 5 in that a single tubular connecting element 61 with accordion-like ends 63 is used in place of the accordion-like connecting elements 45 and hollow bladder element 47. In FIG. 9, the tubular members 65 are triangular-shaped (only one is shown); in FIG. 10, the tubular members 67 are square-shaped (only one is shown); in FIG. 11, the tubular members 69 are hexagonal-shaped (only one is shown); in FIG. 12, the tubular members 71 are circular-shaped (only one is shown); and in FIG. 13, the tubular members 73 are trapezoidal-shaped (only one is shown). The accordion-like connecting elements 45 are extensible and function to allow device 41 to fit and to be adjusted for variations in anatomical size differences and distances between the bony prominences of the scapulae, as similarly function the accordion-like ends 63.

Figure 14:
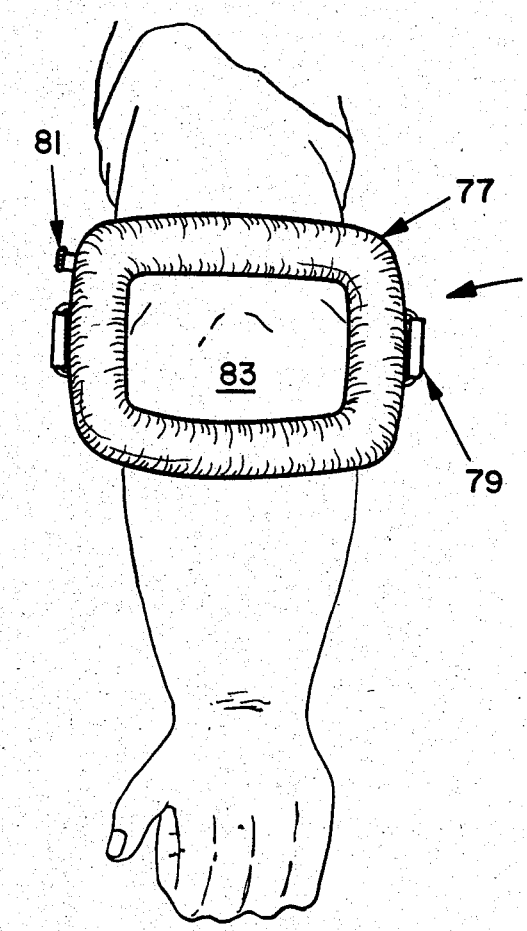
FIG. 14 is a front view of the device for the elbow area with the tubular members being rectangular-shaped.

In FIG. 14 of the drawings, reference numeral 75 generally refers to the therapeutic device for use on the elbow for the prevention and treatment of ulcerations. Device 75 has a rectangular-shaped tubular member 77 with an adjustable attachment element 79 of strip webbing with Velcro fasteners (not shown) suitably affixed to the tubular member 77 and disposed in mounting relationship around the elbow, as shown, with adjustment provided by such Velcro fasteners. Valve 81 allows inflation of tubular member 77.

Tubular member 77 surrounds the bony prominence of the elbow area and continuously makes contact with a second area adjacent to and surrounding the immediate area 83 of such bony prominence of the elbow area and thereby transfers and spreads to such second contact area the pressures created and caused by direct contact with an object, such as a bed, wheel chair, furniture, etc. to thereby prevent ulcerations from developing which would otherwise develop from contact of such object with such bony prominence and the immediate area 83 of such prominence. Hence, with therapeutic device 75 emplaced and worn by a patient, no ulcerations in the elbow area can be caused by contact pressure from an object. Similarly, therapeutic device 75 can be utilized for the treatment of ulcerations theretofore developed by a patient.

Figure 15:
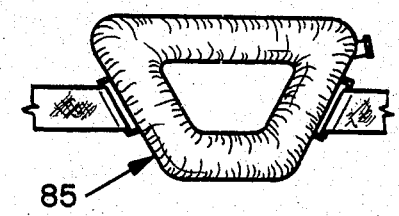
FIG. 15 shows the tubular member of FIG. 14 as being trapezoidal-shaped.
Figure 16:
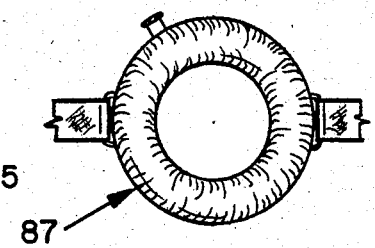
FIG. 16 shows the tubular member of FIG. 14 as being circular-shaped.
Figure 17:
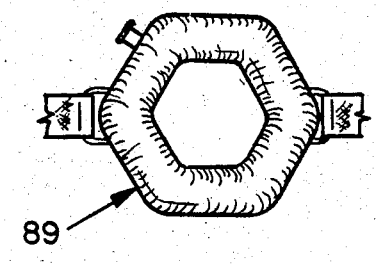
FIG. 17 shows the tubular member of FIG. 14 as being hexagonal-shaped.
Figure 18:
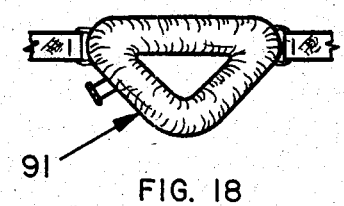
FIG. 18 shows the tubular member of FIG. 14 as being triangular-shaped.
Figure 19:
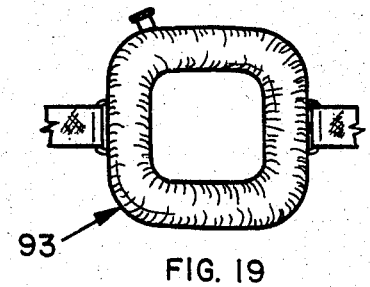
FIG. 19 shows the tubular member of FIG. 14 as being square-shaped.

FIGS. 15-19 of the drawings differ from the therapeutic device 75 shown and described in FIG. 14 in that the shape of the tubular member has been changed to functionally and spatially accommodate the differences in the configuration of the bony prominence in the immediate area 83. In FIG. 15, a trapezoidal-shaped tubular member 85 is used in place of the tubular member 77; in FIG. 16, a circular-shaped tubular member 87 is used; in FIG. 17, a hexagonal-shaped tubular member 89 is used; in FIG. 18, a triangular-shaped tubular member 91 is used; and in FIG. 19, a square-shaped tubular member 93 is used.

Having thusly described my inventions, I claim:

1. A therapeutic device for use in the coccygeal and hip areas of a patient for the prevention and treatment of ulcerations which appear and develop at the bony prominences of the patient's said coccygeal and hip areas and the immediate areas of said bony prominences, said ulcerations being caused by the pressure from an object making direct contact with said bony prominences and their said immediate areas; said therapeutic device comprising tubular members, tubular connecting elements and adjustable attachment elements; one of said tubular members surrounding and continuously making contact with a second area that is adjacent to and surrounds said immediate area of said bony prominence of said coccygeal area, two of said tubular members surrounding and continuously making contact with second areas that are adjacent to and surround said immediate areas of said bony prominences of said hip area, one of said tubular connecting elements being connected to and in communicating relationship with said tubular members disposed in said hip area, a second tubular connecting element being connected to and in communicating relationship with one of said tubular members in said hip area and said tubular member disposed in said coccygeal area, a third tubular connecting element being connected to and in communicating relationship with the second of said tubular members in said hip area and said tubular member in said coccygeal area, said tubular members carrying said adjustable attachment elements for disposing and mounting said device about the hip and coccygeal areas of the patient.

2. A therapeutic device in accordance with claim 1, wherein said tubular members are circular-shaped.

3. A therapeutic device in accordance with claim 2, wherein said tubular member in said coccygeal area is triangular-shaped.

4. A therapeutic device in accordance with claim 2, wherein said tubular member in said coccygeal area is square-shaped.

5. A therapeutic device in accordance with claim 2, wherein said tubular member in said coccygeal area is hexagonal-shaped.

6. A therapeutic device in accordance with claim 2, wherein said tubular member in said coccygeal area is trapezoidal-shaped.

7. A therapeutic device in accordance with claim 1, wherein said tubular connecting elements have accordion-like ends allowing fit and adjustment of said device for variations of the patient's anatomy.

8. A therapeutic device in accordance with claim 1, wherein is further provided a bladder element, said bladder element allowing said device to seat itself over and fitting the natural contours of the buttocks region of the patient with comfort along with securement.

9. A therapeutic device in accordance with claim 8, wherein are further provided accordion-like webbing connecting said bladder element to said tubular members and said tubular connecting elements.

10. A therapeutic device in accordance with claim 8, wherein are provided accordion-like tubular connecting elements connecting said bladder element to one of said tubular connecting elements, connecting said bladder element to one of said tubular members, and with said accordion-like tubular connecting elements establishing communication between said bladder element and said tubular connecting element, and establishing communication between said bladder element and said tubular member.

11. A therapeutic device for use in the scapular area of a patient for the prevention and treatment of ulcerations which appear and develop at the bony prominences of the patient's said scapular area and the immediate areas of said bony prominences, said ulcerations being caused by the pressure from an object making direct contact with said bony prominences and their said immediate areas; said therapeutic device comprising two tubular members, tubular connecting element means and adjustable attachment elements; said tubular members surrounding and continuously making contact with second areas that are adjacent to and surround the respective immediate areas of said bony prominences of said scapular area, said tubular connecting element means being connected to and in communicating relationship with said tubular members disposed in said scapular area, said tubular members carrying said adjustable attachment elements for disposing and mounting said device about the scapular area of the patient.

12. A therapeutic device in accordance with claim 11, wherein said tubular members are circular-shaped.

13. A therapeutic device in accordance with claim 11, wherein said tubular members are square-shaped.

14. A therapeutic device in accordance with claim 11, wherein said tubular members are triangular-shaped.

15. A therapeutic device in accordance with claim 11, wherein said tubular members are hexagonal-shaped.

16. A therapeutic device in accordance with claim 11, wherein said tubular members are trapezoidal-shaped.

17. A therapeutic device in accordance with claim 11, wherein said tubular connecting element means has accordion-like ends allowing fit and adjustment of said device for variations in anatomical size differences and distances between the bony prominences of the scapulae.

18. A therapeutic device in accordance with claim 11, wherein is further provided a bladder element filling the natural dell between the scapulae.

19. A therapeutic device in accordance with claim 18, wherein said tubular connecting element means are accordion-like connecting elements, said accordion-like tubular connecting elements being interposed between said tubular members and said bladder element and establishing communication between said tubular members and said bladder element.

* * * * *